United States Patent
Takahashi

(10) Patent No.: US 11,911,350 B2
(45) Date of Patent: Feb. 27, 2024

(54) REDUCED COENZYME $Q_{10}$-CONTAINING COMPOSITION AND METHOD FOR PRODUCING SAME

(71) Applicant: Petroeuroasia Co., Ltd., Shizuoka (JP)

(72) Inventor: Hidehiro Takahashi, Shizuoka (JP)

(73) Assignee: Petroeuroasia Co., Ltd., Shizuoka (JP)

( * ) Notice: Subject to any disclaimer, the term of this patent is extended or adjusted under 35 U.S.C. 154(b) by 588 days.

(21) Appl. No.: 16/976,616

(22) PCT Filed: Feb. 15, 2019

(86) PCT No.: PCT/JP2019/005516
§ 371 (c)(1),
(2) Date: Aug. 28, 2020

(87) PCT Pub. No.: WO2019/167663
PCT Pub. Date: Sep. 6, 2019

(65) Prior Publication Data
US 2021/0046020 A1 Feb. 18, 2021

(30) Foreign Application Priority Data
Feb. 28, 2018 (JP) ................................. 2018-034461

(51) Int. Cl.
| | | |
|---|---|---|
| *A61L 31/12* | (2006.01) | |
| *A61K 31/122* | (2006.01) | |
| *A61K 9/16* | (2006.01) | |
| *A61K 31/375* | (2006.01) | |

(52) U.S. Cl.
CPC .......... *A61K 31/122* (2013.01); *A61K 9/1652* (2013.01); *A61K 31/375* (2013.01)

(58) Field of Classification Search
CPC ...... A61K 31/22; A61K 9/1652; A61K 8/355; A61K 31/122
See application file for complete search history.

(56) References Cited

U.S. PATENT DOCUMENTS

| | | |
|---|---|---|
| 2007/0243180 A1 | 10/2007 | Tanaka et al. |
| 2008/0248013 A1 | 10/2008 | Ikemoto et al. |
| 2017/0231926 A1 | 8/2017 | Kuriki et al. |

FOREIGN PATENT DOCUMENTS

| | | | |
|---|---|---|---|
| CN | 106619588 | * | 5/2017 |
| CN | 106619588 A | | 5/2017 |
| EP | 1681053 | | 7/2006 |
| EP | 2995605 | | 1/2017 |
| JP | 2008-297237 | | 12/2008 |
| JP | 2008-297237 A | * | 12/2008 |
| JP | 2010-126492 | | 6/2010 |
| WO | WO 2005/041945 A1 | | 5/2005 |
| WO | 2006/022187 A1 | * | 3/2006 |
| WO | 2006/022871 A1 | * | 3/2006 |
| WO | WO 2006/022187 A1 | | 3/2006 |
| WO | WO 2007/080787 A1 | | 7/2007 |

OTHER PUBLICATIONS

International Search Report issued in application No. PCT/JP2019/005516 dated Mar. 26, 2019.
Extended European Search Report issued in EP Application No. 19760082.8, dated Sep. 29, 2021.
International Preliminary Report on Patentability issued in PCT Application No. PCT/JP2019/005516, dated Sep. 1, 2020.

* cited by examiner

*Primary Examiner* — Carlos A Azpuru
(74) *Attorney, Agent, or Firm* — Knobbe, Martens, Olson & Bear, LLP

(57) ABSTRACT

A reduced coenzyme $Q_{10}$-containing composition has high water solubility and excellent storage stability. A powder composition contains the reduced coenzyme $Q_{10}$, starch octenylsuccinate, and gum Arabic. A method of producing the powder composition includes homogenizing the ingredients in water to obtain an emulsion composition; and drying the composition.

9 Claims, No Drawings

REDUCED COENZYME $Q_{10}$-CONTAINING COMPOSITION AND METHOD FOR PRODUCING SAME

CROSS-REFERENCE TO RELATED APPLICATION

The present application enjoys the benefit of priority to Japanese Patent Application No. 2018-34461 (filed on Feb. 28, 2018), the entire disclosure of which is herein incorporated by reference.

TECHNICAL FIELD

The present invention relates to a reduced coenzyme $Q_{10}$-containing composition and a method of producing the same, particularly to a water-dispersible reduced coenzyme $Q_{10}$-containing powder composition and a method of producing the same.

BACKGROUND ART

Coenzyme $Q_{10}$, a lipid-soluble component of the respiratory chain and the electron transport chain of photosynthesis, plays a mediating role for the electron transfer between redox proteins in biological membranes. Especially in mammals including human, coenzyme $Q_{10}$ localizes in organelles such as mitochondria, lysosomes, and Golgi bodies, and is involved, as a component of the electron transport chain, in ATP production-activating and biological antioxidative actions and in membrane stabilization. That is, coenzyme $Q_{10}$ is a coenzyme that is closely involved in biological energy production, and is also considered as a substance essential for the maintenance of biological functions. Thus, coenzyme $Q_{10}$ has been widely used as an ingredient for various applications, including pharmaceutical products, dietary supplements, cosmetics, and the like.

Coenzyme $Q_{10}$ is present in the oxidized and reduced forms and coenzyme $Q_{10}$ in biological bodies is mostly present in the form of reduced coenzyme $Q_{10}$. Reduced coenzyme $Q_{10}$ has antioxidant properties and is recently reported to be more effective in various applications than oxidized coenzyme $Q_{10}$.

However, enhancing the solubility of coenzyme $Q_{10}$ in water has been a challenge related to the practical use of coenzyme $Q_{10}$ in pharmaceutical products, food products, cosmetics, and the like because coenzyme $Q_{10}$ is poorly soluble in water. A water-soluble inclusion compound of coenzyme $Q_{10}$ obtained by treatment with cyclodextrin has been previously reported (Patent Documents 1 and 2).

REFERENCE LIST

Patent Documents

Patent Document 1: WO 2005/041945
Patent Document 2: JP 2010-126492 A

SUMMARY OF THE INVENTION

A reduced coenzyme $Q_{10}$-cyclodextrin inclusion complex prepared according to Patent Document 1 led to only unsatisfactory results in terms of water solubility and storage stability (data not shown). That is, there remains a need for a reduced coenzyme $Q_{10}$-containing powder composition with high water solubility and excellent storage stability.

An object of the present invention is to provide a reduced coenzyme $Q_{10}$-containing composition with high water solubility and excellent storage stability and a method of producing the same.

The present invention provides the following inventions.

[1] A powder composition including (A) reduced coenzyme $Q_{10}$, (B) starch octenylsuccinate or a salt thereof, and (C) gum arabic.
[2] The composition according to [1], which comprises (B) starch octenylsuccinate or a salt thereof at a ratio of at least 0.5 (mass ratio in terms of solid content) with respect to (A) reduced coenzyme $Q_{10}$ (1).
[3] The composition according to [1] or [2], which comprises (C) gum arabic at a ratio of 0.125 to 1 (mass ratio in terms of solid content) with respect to (A) reduced coenzyme $Q_{10}$ (1).
[4] The composition according to any one of [1] to [3], which further comprises (D) an antioxidant.
[5] The composition according to [4], which comprises (D) the antioxidant at a ratio of 0.125 to 1 (mass ratio in terms of solid content) with respect to (A) reduced coenzyme $Q_{10}$ (1).
[6] The composition according to [4] or [5], wherein the antioxidant is ascorbic acid.
[7] A reduced coenzyme $Q_{10}$-containing solid formulation, comprising the composition according to any one of [1] to [6].
[8] The solid formulation according to [7], which is in the form of tablet, capsule, or powder.
[9] A method of producing the composition according to any one of [1] to [6], including the steps of homogenizing (A) reduced coenzyme $Q_{10}$, (B) starch octenylsuccinate or a salt thereof, and (C) gum arabic in water to obtain an emulsion composition, and drying the composition.

The composition according to the present invention can allow reduced coenzyme $Q_{10}$, which is poorly soluble in water, to disperse easily in water, and further exhibits excellent dissolution stability. Thus, an advantage of the present invention is that the present invention can facilitate the usage of reduced coenzyme $Q_{10}$ in pharmaceutical products, food products, cosmetics, and the like. Additionally, because starch octenylsuccinate or a salt thereof and gum arabic are approved for use in food products and are not allergenic, the composition of the present invention and food products or the like including the same can be consumed without safety concerns, which is another advantage of the present invention.

DETAILED DESCRIPTION OF THE PREFERRED EMBODIMENT

The composition according to the present invention is a powder composition comprising (A) reduced coenzyme $Q_{10}$, (B) starch octenylsuccinate or a salt thereof, and (C) gum arabic.

(A) Reduced Coenzyme $Q_{10}$

Reduced coenzyme $Q_{10}$ incorporated in the composition of the present invention can be prepared by any known technique, such as chemical synthesis, isolation from a microorganism culture (fermentation), or extraction from natural products, and preferably by reducing oxidized coenzyme $Q_{10}$, such as existing high-purity coenzyme $Q_{10}$ products, or a mixture of oxidized coenzyme $Q_{10}$ and reduced coenzyme $Q_{10}$ with a commonly used reducing agent, such as sodium hyposulfite, sodium borohydride, or ascorbic acid.

The content of reduced coenzyme $Q_{10}$ in the composition of the present invention is, for example, from 1.0 to 50% by mass (in terms of solid content), preferably from 5.0 to 40% by mass (in terms of solid content).

(B) Starch Octenylsuccinate

Starch octenylsuccinate incorporated in the composition of the present invention is an excipient or emulsifier which is approved for use in pharmaceutical products, food products, cosmetics, and the like, and any commercially available starch octenylsuccinate may be used. Starch octenylsuccinate incorporated in the composition of the present invention may be in the form of a salt (preferably a salt acceptable for pharmaceutical products, food products, cosmetics, and the like). The salt of starch octenylsuccinate includes sodium starch octenylsuccinate.

In the present invention, starch octenylsuccinate or a salt thereof may be incorporated as an excipient or an emulsifier. Any excipient or emulsifier other than starch octenylsuccinate may further be incorporated in the composition of the present invention, provided that no reduction in water solubility and storage stability occurs in the resulting composition. Any excipient acceptable for pharmaceutical products, food products, cosmetics, and the like can be used as an excipient that may be incorporated in the composition of the present invention, and examples of the excipient include starch, modified starch, saccharides, and cellulose. Among those, starch includes corn starch, wheat starch, and potato starch; and modified starch includes dextrin, maltodextrin, powdered corn syrup, and solubilized starch. Moreover, saccharides include monosaccharides and disaccharides (for example, lactose, xylose) and also include sugar alcohols (for example, xylitol, maltitol, inositol). Additionally, any emulsifier acceptable for pharmaceutical products, food products, cosmetics, and the like can be used as an emulsifier that may be incorporated in the composition of the present invention, and examples of the emulsifier include various saponins, lecithins, enzymatically treated lecithins, enzymatically degraded lecithins, glycerol esters, phytosterols, and sucrose fatty acid esters, and the emulsifier can be added in an amount that will not prevent emulsification and/or dehydration of the composition of the present invention.

The minimum content of starch octenylsuccinate or a salt thereof in the composition of the present invention may be at a ratio of 0.5 (preferably 0.8) with respect to the content of reduced coenzyme $Q_{10}$ (1) (mass ratio in terms of solid content). The maximum content of starch octenylsuccinate or a salt thereof in the composition of the present invention is not specifically limited but can be at a ratio of, for example, 5, 2, or 1.5 with respect to the content of reduced coenzyme $Q_{10}$ (1) (mass ratio in terms of solid content). The minimum contents may arbitrarily be combined with the maximum contents, and the above ratio may range, for example, from 0.5 to 5 or from 0.8 to 5.

(C) Gum Arabic

Gum arabic incorporated in the composition of the present invention is a thickener which is approved for use in pharmaceutical products, food products, cosmetics, and the like, and any commercially available gum arabic may be used. Gum arabic includes demineralized and unmodified types of gum arabic, both of which may be incorporated in the composition of the present invention.

In the present invention, gum arabic may be incorporated as a thickener. Any thickener other than gum arabic may further be incorporated in the composition of the present invention, provided that no reduction in water solubility and storage stability occurs in the resulting composition. Any thickener acceptable for pharmaceutical products, food products, cosmetics, and the like may be used, and examples of such a thickener include arabinogalactan, alginate, welan gum, elemi resin, *Artemisia sphaerocephala* seed gum, curdlan, cassia gum, sodium caseinate, carrageenan, karaya gum, carob bean gum, xanthan gum, chitin, chitosan, guar gum, glucosamine, psyllium seed gum, gellan gum, tamarind gum, *Abelmoschus manihot*, tragacanth gum, *Bacillus natto* gum, furcellaran, pullulan, pectin, macrophomopsis gum, methylcellulose, and *Gloiopeltis furcata* extract.

The minimum and maximum contents of gum arabic in the composition of the present invention may be at a ratio of 0.125 (preferably 0.2) and at a ratio of 1 (preferably 0.5) with respect to the content of reduced coenzyme $Q_{10}$ (1) (mass ratio in terms of solid content), respectively. The minimum contents may arbitrarily be combined with the maximum contents, and the above ratio may range, for example, from 0.125 to 1 or from 0.2 to 0.5.

(D) Antioxidant

In the present invention, one, two, or more types of antioxidants can be used to prevent, for example, degradation of reduced coenzyme $Q_{10}$ included in the composition of the present invention. Any antioxidant acceptable for pharmaceutical products, food products, cosmetics, and the like can be used in the present invention, and examples of such an antioxidant include ascorbic acid and esters and salts thereof, sodium sulfite, calcium disodium ethylenediaminetetraacetate, disodium ethylenediaminetetraacetate, L-cysteine chloride, dibutylhydroxytoluene, d-α-tocopherol acetate, d-tocopherols, tocotrienol, mixed tocopherols, catechin, quercetin, rutin, ferulic acid, gallic acid, rice bran oil extract, sage extract, green coffee bean extract, sunflower seed extract, grape seed extract, sesame oil unsaponifiable matter, tea extract, propolis extract, *Morella rubra* extract, hego-gingko leaf extract, and *Styphnolobium japonicum* extract. Among those, ascorbic acid and esters and salts thereof include L-ascorbic acid, L-ascorbic acid esters, sodium L-ascorbate, and L-ascorbyl palmitate. In the present invention, ascorbic acid and/or a salt thereof can be suitably used as an antioxidant.

The minimum and maximum contents of the antioxidant in the composition of the present invention may be at a ratio of 0.125 (preferably 0.25) and at a ratio of 1 (preferably 0.75) with respect to the content of reduced coenzyme $Q_{10}$ (1) (mass ratio in terms of solid content), respectively. The minimum contents may arbitrarily be combined with the maximum contents, and the above ratio may range, for example, from 0.125 to 1 or from 0.25 to 0.75.

The composition of the present invention may comprise the above component (D), in addition to the above components (A), (B), and (C), and may further comprise any component acceptable for pharmaceutical products, food products, cosmetics, and the like, other than the above components (A), (B), (C), and (D), and examples of such components include flavoring agents, preservatives, sweetening agents, and coloring agents.

The composition of the present invention can be produced by homogenizing the ingredients, as described below. Thus, the composition of the present invention can contain the above components (A), (B), and (C), and optionally the above component (D) and any other components in a homogenized form.

The composition of the present invention is also a dried emulsion composition that is obtained by drying a reduced coenzyme $Q_{10}$-containing emulsion composition and is dispersible in water. In this respect, whether or not the composition is "dispersible in water" can be evaluated by introducing 0.2 g (in terms of solid content) of the composition into 100 mL of water at room temperature, stirring the mixture, and visually observing the appearance of the resulting solution. Specifically, full dissolution of the introduced composition in water without suspended and/or precipitated matters makes the composition considered as "water-dispersible." As used herein, the phrases "dissolution in water" and "water solubility" mean "dispersion in water" and "water dispersibility."

The composition of the present invention is a water-dispersible reduced coenzyme $Q_{10}$-containing composition and can thus be added as an ingredient to foods, to produce food products with homogeneously incorporated reduced coenzyme $Q_{10}$. Besides being added to foods, the composition of the present invention can also be added as an ingredient to feeds or pet foods, to produce feed and pet food products with homogeneously incorporated reduced coenzyme $Q_{10}$. That is, food, feed, and pet food products each comprising the composition of the present invention are provided by the present invention.

The foods that can include the composition of the present invention are not specifically limited but include water (for example, drinking water, hydrogen water, mineral water, flavored water), soft drinks (for example, fruit juices, vegetable juices, mixed fruit and vegetable juices, carbonated drinks, functional beverages, sports drinks, non-alcoholic drinks), tea drinks (for example, green tea, black tea, Chinese tea, barley tea, buckwheat tea, mate, blended tea drinks), coffee drinks (for example, canned coffee, instant coffee), cocoa drinks, fermented milk drinks, green vegetable juices, soy milk drinks, milk products (for example, cow milk, milk drinks, processed milk, yogurt), nutritional supplement drinks, jelly beverages, soups, alcoholic drinks (for example, beer, low-malt beer, whisky, bourbon whiskey, spirits, liqueur, wine, fruit wine, sake, shochu, other liquors), carbohydrate-containing foods (for example, cooked rice, noodles, bread, pasta), western cakes (for example, biscuit, cracker, cookie, waffle, pie), Japanese cakes (for example, rice cracker, sweet bun, sweet bean jelly), chewing gum, candy, and frozen sweets (for example, ice cream and sherbet).

Additionally, the foods to which the composition of the present invention can be incorporated may be in the form of liquid, such as the form of beverage and/or liquid diet, or in the form of paste, semi-solid, or gel, or in the form of solid or powder. Because the composition of the present invention is excellent not only in water solubility but also in dissolution stability in water, any foods or cosmetics including the composition of the present invention can be advantageously provided in the form of beverages or water-based cosmetics despite of the presence of reduced coenzyme $Q_{10}$, which is poorly soluble in water. Moreover, because the composition of the present invention is stable even if the composition is compressed into tablets on a tablet press, any pharmaceutical products and/or dietary supplements including the composition of the present invention can advantageously be provided in the form of solid preparations, such as tablets, capsules, and powders.

The amount of the composition of the present invention incorporated into food products according to the present invention can be determined based on the daily intake of reduced coenzyme $Q_{10}$. That is, the composition of the present invention can be incorporated into any food product according to the present invention in such a manner that the effective daily intake of reduced coenzyme $Q_{10}$ for human can be consumed from the food product, where the effective daily intake for human is from 3 to 300 mg (preferably 10 to 100 mg). In this case, the food product according to the present invention may be packaged in such a manner that the effective daily intake of reduced coenzyme $Q_{10}$ can be consumed from the food product, where the packaging format may be a single-dose packaging or multi-dose packaging format as long as the effective daily intake can be consumed. In cases where the food product is provided in a packaged form, it is desirable that a description of the intake be printed on the package or a document describing the intake be provided as a package insert, to facilitate consumption of the effective daily intake. Moreover, in cases where the effective daily intake is provided in a multi-dose packaging format, a set of multiple packages each containing the effective daily intake can also be provided for ease of consumption.

The composition of the present invention can be produced by homogenizing the ingredients and drying a resulting emulsion composition.

Homogenization of the ingredients can be performed by first adding ingredients including reduced coenzyme $Q_{10}$, starch octenylsuccinate or a salt thereof, and gum arabic to water and stirring the resulting mixture, optionally further adding an antioxidant(s) and any other components to the mixture and stirring the resulting mixture, and then homogenizing the resulting mixture.

The homogenization is a process to reduce and homogenize the sizes of ingredient particles contained in the mixture solution. The homogenization can be performed on a homogenizer (for example, Milder (manufactured by Pacific Machinery & Engineering Co., Ltd.), Silverson homogenizer (manufactured by Silverson Japan)), high-pressure homogenizer (for example, homogenizer (manufactured by Sanwa Engineering Ltd.), high-pressure homogenizer (manufactured by Sanmaru Machinery Co., Ltd.)), or the like. When a homogenizer is used, a condition of 25 to 40 m/s can be used for homogenization. In addition, when a high-pressure homogenizer is used, a condition of 50 to 150 MPa can be used for homogenization, or a higher pressure may be applied in homogenization. A reduced coenzyme $Q_{10}$-containing emulsion composition can be obtained after homogenization, in which reduced coenzyme $Q_{10}$ is in a homogenized form, namely a dispersed form in water.

Drying of the emulsion composition can be performed by any known method, such as spray drying or lyophilization. A reduced coenzyme $Q_{10}$-containing powder composition can be obtained after drying, in which reduced coenzyme $Q_{10}$ and the other components are contained in a homogenized form.

EXAMPLES

The present invention will be described in more specific detail with reference to the following examples, but the present invention is not limited by these examples.

Example 1: Assessment of Emulsifiers for the Production of Reduced Coenzyme $Q_{10}$-Containing Powder Compositions Emulsifiers were assessed for the production of water-dispersible reduced coenzyme $Q_{10}$-containing powder compositions. Specifically, 10 g of each of the following emulsifiers (A1 to A15) was individually added to 100 mL of water together with 2.5 g of gum arabic (Inagel, manufactured by Ina Food Industry Co., Ltd.), and the resulting mixtures were then heated to 80° C. To each mixture, 20 g of reduced coenzyme $Q_{10}$ (manufactured by Kaneka Corporation) was added and then mixed. Subsequently, the mixtures were emulsified using an ultrasonic oscillator (manufactured by SONICS & MATERIALS Inc.; at 20 kHz for 15 min twice). The emulsions were dried using a freeze dryer (FDU-2200, manufactured by EYELA Co., Ltd.) according to a routine procedure, and the resulting dry matters were finely ground with a compact and powerful mill (ForceMill, manufactured by Osaka Chemical Co., Ltd.) to prepare reduced coenzyme $Q_{10}$-containing dry powder formulations.

<Emulsifiers>
A1: Lecithin (SLP-White Lyso, manufactured by Tsuji Oil Mills Co., Ltd.)
A2: Propylene glycol alginate (DUCK LOID, manufactured by Kikkoman Biochemifa Company)
A3: Polyoxyethylenesorbitan fatty acid ester (Polysorbate 80, manufactured by NOF Corporation)
A4: Glycerol fatty acid ester (Sunsoft No. 118, manufactured by Taiyo Kagaku Co., Ltd.)
A5: Sucrose fatty acid ester (S-170, manufactured by Mitsubishi-Chemical Foods Corporation)
A6: Sucrose fatty acid ester (S-970, manufactured by Mitsubishi-Chemical Foods Corporation)
A7: Sucrose fatty acid ester (S-1670, manufactured by Mitsubishi-Chemical Foods Corporation)
A8: Polyglycerol fatty acid ester (Sunsoft Q-18S, manufactured by Taiyo Kagaku Co., Ltd.)
A9: Propylene glycol fatty acid ester (Sunsoft No. 25CD, manufactured by Taiyo Kagaku Co., Ltd.)
A10: Sorbitan fatty acid ester (Sunsoft No. 61S, manufactured by Taiyo Kagaku Co., Ltd.)
A11: Sodium starch octenylsuccinate (Emulstar 500A, manufactured by Matsutani Chemical Industry Co., Ltd.)
A12: Sodium starch octenylsuccinate (Emulstar 500, manufactured by Matsutani Chemical Industry Co., Ltd.)
A13: Sodium starch octenylsuccinate (CAPSUL, manufactured by Ingredion Japan K.K.)
A14: Sodium starch octenylsuccinate (PURITY GUM BE, manufactured by Ingredion Japan K.K.)
A15: Carboxymethylcellulose (Sunrose SLD, manufactured by Nippon Paper Industries Co., Ltd.)

Each obtained reduced coenzyme $Q_{10}$-containing dry powder formulation was evaluated for the powder appearance, the water solubility, and the stability after dissolution in water and subsequent 8-hour standing. The powder appearance, the water solubility, and the stability after dissolution in water and subsequent 8-hour standing were classified into three grades (A: excellent, B: normal, C: bad) by visual observation. For the water solubility, a powder formulation observed to produce a solution with some suspended matters was graded B, and a powder formulation observed to produce a solution with a ring of oil was graded C. For the stability after dissolution in water and subsequent 8-hour standing, a powder formulation observed to produce a solution retaining the properties at the time of dissolution was graded A, and a powder formulation observed to produce a solution with some suspended matters was graded B, and a powder formulation observed to produce a solution with a ring of oil was graded C. Moreover, the water solubility and the stability after dissolution in water and subsequent 8-hour standing were examined by adding 0.2 g of each reduced coenzyme $Q_{10}$-containing powder formulation to 100 mL of water at room temperature, stirring the mixture, and then observing the resulting mixture.

The results were as shown in Table 1.

TABLE 1

Evaluation of characteristics and solubility in reduced coenzyme $Q_{10}$-containing powder compositions

| Test sample | Powder appearance | Water solubility | Stability after dissolution in water and subsequent 8-hour standing |
|---|---|---|---|
| A1 | C | C | C |
| A2 | C | C | C |
| A3 | C | B | C |
| A4 | C | B | C |
| A5 | C | C | C |
| A6 | C | C | C |
| A7 | C | C | C |
| A8 | C | B | C |
| A9 | C | C | C |
| A10 | C | C | C |
| A11 | A | A | A |
| A12 | A | A | A |
| A13 | A | A | A |
| A14 | A | A | A |
| A15 | B | B | C |

As seen above, only the reduced coenzyme $Q_{10}$-containing powder compositions comprising sodium starch octenylsuccinate, among those emulsifiers A1 to 15, were excellent not only in powder appearance and water solubility but also in dissolution stability.

Example 2: Production and Evaluation of Reduced Coenzyme $Q_{10}$-Containing Powder Compositions (1)

Reduced coenzyme $Q_{10}$-containing powder compositions comprising the components as indicated in Table 2 below were produced. That is, all the components for each test sample were added to and dissolved with stirring in 500 mL of water heated at 80° C. After the dissolution, the mixtures were emulsified using an ultrasonic oscillator (manufactured by SONICS & MATERIALS Inc.; at 20 kHz for 15 min twice). The emulsions were dried using a freeze dryer (FDU-2200, manufactured by EYELA Co., Ltd.) according to a routine procedure, and the resulting dry matters were finely ground with a compact and powerful mill (ForceMill, manufactured by Osaka Chemical Co., Ltd.) to prepare reduced coenzyme $Q_{10}$-containing dry powder formulations.

TABLE 2

Reduced coenzyme Q₁₀-containing powder compositions (Example 2)

| Test sample | Reduced coenzyme $Q_{10}$ (g) | Sodium starch octenylsuccinate Emulstar 500A (low viscosity) (g) | Emulstar 500 (high viscosity) (g) | CAPSUL (low viscosity) (g) | PURITY GUM BE (high viscosity) (g) | Gum arabic Inagel (unmodified type) (g) | San-Arabic (demineralized type) (g) | Sodium ascorbate (g) |
|---|---|---|---|---|---|---|---|---|
| 1 | 20 | 5 | | | | 5 | | |
| 2 | 20 | 10 | | | | 5 | | |
| 3 | 20 | 20 | | | | 5 | | |
| 4 | 20 | 30 | | | | 5 | | |
| 5 | 20 | | 5 | | | 5 | | |
| 6 | 20 | | 10 | | | 5 | | |
| 7 | 20 | | 20 | | | 5 | | |
| 8 | 20 | | 30 | | | 5 | | |
| 9 | 20 | | | 5 | | 5 | | |
| 10 | 20 | | | 10 | | 5 | | |
| 11 | 20 | | | 20 | | 5 | | |
| 12 | 20 | | | 30 | | 5 | | |
| 13 | 20 | | | | 5 | 5 | | |
| 14 | 20 | | | | 10 | 5 | | |
| 15 | 20 | | | | 20 | 5 | | |
| 16 | 20 | | | | 30 | 5 | | |
| 17 | 20 | 20 | | | | 0 | | |
| 18 | 20 | 20 | | | | 2.5 | | |
| 19 | 20 | 20 | | | | 7.5 | | |
| 20 | 20 | 20 | | | | 10 | | |
| 21 | 20 | 20 | | | | | 2.5 | |
| 22 | 20 | 20 | | | | | 5 | |
| 23 | 20 | 20 | | | | | 7.5 | |
| 24 | 20 | 20 | | | | | 10 | |
| 25 | 20 | | 20 | | | 0 | | |
| 26 | 20 | | 20 | | | 2.5 | | |
| 27 | 20 | | 20 | | | 7.5 | | |
| 28 | 20 | | 20 | | | 10 | | |
| 29 | 20 | | | 20 | | 0 | | |
| 30 | 20 | | | 20 | | 2.5 | | |
| 31 | 20 | | | 20 | | 7.5 | | |
| 32 | 20 | | | 20 | | 10 | | |
| 33 | 20 | | | | 20 | 0 | | |
| 34 | 20 | | | | 20 | 2.5 | | |
| 35 | 20 | | | | 20 | 7.5 | | |
| 36 | 20 | | | | 20 | 10 | | |
| 37 | 20 | | | 20 | | | 2.5 | |
| 38 | 20 | | | 20 | | | 5 | |
| 39 | 20 | | | 20 | | | 7.5 | |
| 40 | 20 | | | 20 | | | 10 | |
| 41 | 20 | 20 | | | | 5 | | 2.5 |
| 42 | 20 | 20 | | | | 5 | | 5 |
| 43 | 20 | 20 | | | | 5 | | 7.5 |
| 44 | 20 | 20 | | | | 5 | | 10 |
| 45 | 20 | 20 | | | | 5 | | 15 |
| 46 | 20 | 20 | | | | | 5 | 2.5 |
| 47 | 20 | 20 | | | | | 5 | 5 |
| 48 | 20 | 20 | | | | | 5 | 7.5 |
| 49 | 20 | 20 | | | | | 5 | 10 |
| 50 | 20 | 20 | | | | | 5 | 15 |

Reduced coenzyme Q₁₀: manufactured by Kaneka Corporation
Emulstar 500A and Emulstar 500: manufactured by Matsutani Chemical Industry Co., Ltd.
CAPSUL and PURITY GUM BE: manufactured by Ingredion Japan K.K.
Inagel: manufactured by Ina Food Industry Co., Ltd.
San-Arabic: manufactured by Sanei-Yakuhin Co., Ltd.
Sodium ascorbate: manufactured by DSM Japan K.K.

Each obtained reduced coenzyme Q₁₀-containing dry powder formulation was evaluated for the powder appearance (characteristics), the water solubility, and the stability after dissolution in water and subsequent 8-hour standing. The powder appearance, the water solubility, and the stability after dissolution in water and subsequent 8-hour standing were classified into three grades (A: excellent, B: normal, C: bad) by visual observation. For the water solubility, a powder formulation observed to produce a solution with some suspended matters was graded B, and a powder formulation observed to produce a solution with a ring of oil was graded C. For the stability after dissolution in water and subsequent 8-hour standing, a powder formulation observed to produce a solution retaining the properties at the time of dissolution was graded A, and a powder formulation observed to produce a solution with some suspended matters was graded B, and a powder formulation observed to produce a solution with a ring of oil was graded C. Moreover, the water solubility and the stability after dissolution in water and subsequent 8-hour standing were examined by adding 0.2 g of each reduced coenzyme $Q_{10}$-containing dry powder formulation to 100 mL of water at room temperature, stirring the mixture, and then observing the resulting mixture.

The results were as shown in Table 3.

TABLE 3

Evaluation of characteristics and solubility in reduced coenzyme $Q_{10}$-containing powder compositions

| Test sample | Powder appearance | Water solubility | Stability after dissolution in water and subsequent 8-hour standing |
|---|---|---|---|
| 1 | C | C | C |
| 2 | A | A | A |
| 3 | A | A | A |
| 4 | A | A | A |
| 5 | B | C | C |
| 6 | B | B | C |
| 7 | A | A | A |
| 8 | A | A | A |
| 9 | B | C | C |
| 10 | A | A | A |
| 11 | A | A | A |
| 12 | A | A | A |
| 13 | C | C | C |
| 14 | C | C | C |
| 15 | B | A | A |
| 16 | A | A | A |
| 17 | B | C | C |
| 18 | A | A | A |
| 19 | A | A | A |
| 20 | A | A | A |
| 21 | B | A | B |
| 22 | A | A | A |
| 23 | A | A | A |
| 24 | A | A | A |
| 25 | C | C | C |
| 26 | B | C | C |
| 27 | A | A | B |
| 28 | A | A | A |
| 29 | C | C | C |
| 30 | B | C | C |
| 31 | A | A | B |
| 32 | A | A | A |
| 33 | C | C | C |
| 34 | B | C | C |
| 35 | B | A | A |
| 36 | A | A | A |
| 37 | C | C | C |
| 38 | B | A | A |
| 39 | B | A | A |
| 40 | A | A | A |
| 41 | A | A | A |
| 42 | A | A | A |
| 43 | A | A | A |
| 44 | A | A | A |
| 45 | A | A | A |
| 46 | A | A | A |
| 47 | A | A | A |
| 48 | A | A | A |
| 49 | A | A | A |
| 50 | A | A | A |

As seen above, the powder compositions comprising a given amount of sodium starch octenylsuccinate with respect to reduced coenzyme $Q_{10}$ were excellent not only in powder appearance and water solubility but also in dissolution stability. Additionally, the powder compositions comprising given amounts of sodium starch octenylsuccinate and also of gum arabic with respect to reduced coenzyme $Q_{10}$ were excellent not only in powder appearance and water solubility but also in dissolution stability.

Moreover, each obtained reduced coenzyme $Q_{10}$-containing dry powder formulation with a weight of 5 g was placed in a glass vial with a volume of 50 mL and stored at 45° C. for evaluation of storage stability. The powder appearance (characteristics), the water solubility, the stability after dissolution in water and subsequent 8-hour standing, and the residual amount of reduced coenzyme $Q_{10}$ were evaluated on Day 14. The powder appearance, the water solubility, and the stability after dissolution in water and subsequent 8-hour standing were classified into three grades (A: excellent, B: normal, C: bad) by visual observation. For the water solubility, a powder formulation observed to produce a solution with some suspended matters was graded B, and a powder formulation observed to produce a solution with a ring of oil was graded C. For the stability after dissolution in water and subsequent 8-hour standing, a powder formulation observed to produce a solution retaining the properties at the time of dissolution was graded A, and a powder formulation observed to produce a solution with some suspended matters was graded B, and a powder formulation observed to produce a solution with a ring of oil was graded C. Moreover, the water solubility and the stability after dissolution in water and subsequent 8-hour standing were examined by adding 0.2 g of each reduced coenzyme $Q_{10}$-containing dry powder formulation to 100 mL of water at room temperature, stirring the mixture, and then observing the resulting mixture. The storage stability of the active ingredient was evaluated based on the content ratio of reduced coenzyme $Q_{10}$ (the content ratio (%) between before and after the storage stability test). The content of reduced coenzyme $Q_{10}$ was measured by high-performance liquid chromatography (HPLC). The conditions for HPLC were as follows.

<HPLC Conditions>
Instrument: Waters Acquity Ultra-Performance Liquid Chromatography System
Column: C18, 2.5 μm, 2.1 mm×100 mm
Flow rate: 0.3 mL/min
Elution: methanol/n-hexane (9:1)
Injection volume: 3 μL
Column temperature: 35° C.
Detection wavelength: 290 nm The results were as shown in Table 4.

TABLE 4

Evaluation of storage stability in reduced coenzyme $Q_{10}$-containing powder compositions

| Test sample | Powder appearance | Water solubility | Stability after dissolution in water and subsequent 8-hour standing | Content ratio of reduced coenzyme $Q_{10}$ (%) |
|---|---|---|---|---|
| 1 | C, Color change to yellow | C | C | 11 |
| 2 | B, Color change to yellow | A | B | 13 |
| 3 | B, Color change to yellow | A | A | 17 |
| 4 | A, Color change to yellow | A | A | 10 |
| 5 | C, Color change to yellow | C | C | 15 |
| 6 | B, Color change to yellow | B | C | 11 |
| 7 | A, Color change to yellow | A | A | 14 |
| 8 | A, Color change to yellow | A | A | 18 |
| 9 | C, Color change to yellow | C | C | 12 |
| 10 | B, Color change to yellow | A | A | 11 |

TABLE 4-continued

Evaluation of storage stability in reduced coenzyme $Q_{10}$-containing powder compositions

| Test sample | Powder appearance | Water solubility | Stability after dissolution in water and subsequent 8-hour standing | Content ratio of reduced coenzyme $Q_{10}$ (%) |
|---|---|---|---|---|
| 11 | B, Color change to yellow | A | A | 15 |
| 12 | A, Color change to yellow | A | A | 16 |
| 13 | C, Color change to yellow | C | C | 14 |
| 14 | C, Color change to yellow | C | C | 10 |
| 15 | B, Color change to yellow | A | A | 11 |
| 16 | A, Color change to yellow | A | A | 16 |
| 17 | C, Color change to yellow | B | C | 10 |
| 18 | C, Color change to yellow | A | A | 14 |
| 19 | B, Color change to yellow | A | A | 12 |
| 20 | A, Color change to yellow | A | A | 11 |
| 21 | C, Color change to yellow | A | B | 14 |
| 22 | C, Color change to yellow | A | A | 10 |
| 23 | B, Color change to yellow | A | A | 11 |
| 24 | A, Color change to yellow | A | A | 12 |
| 25 | C, Color change to yellow | C | C | 11 |
| 26 | C, Color change to yellow | C | C | 13 |
| 27 | B, Color change to yellow | A | B | 15 |
| 28 | A, Color change to yellow | A | A | 12 |
| 29 | C, Color change to yellow | C | C | 14 |
| 30 | C, Color change to yellow | C | C | 12 |
| 31 | A, Color change to yellow | A | B | 11 |
| 32 | A, Color change to yellow | A | A | 17 |
| 33 | C, Color change to yellow | C | C | 12 |
| 34 | C, Color change to yellow | C | C | 14 |
| 35 | B, Color change to yellow | A | A | 11 |
| 36 | A, Color change to yellow | A | A | 15 |
| 37 | C, Color change to yellow | C | C | 12 |
| 38 | C, Color change to yellow | A | A | 10 |
| 39 | B, Color change to yellow | A | A | 14 |
| 40 | A, Color change to yellow | A | A | 13 |
| 41 | A, Color change to pale yellow | A | A | 78 |
| 42 | A, No color change | A | A | 90 |
| 43 | A, No color change | A | A | 91 |
| 44 | A, No color change | A | A | 92 |
| 45 | A, No color change | A | A | 92 |
| 46 | A, Color change to a yellowish color | A | A | 71 |
| 47 | A, Color change to pale yellow | A | A | 80 |
| 48 | A, No color change | A | A | 90 |
| 49 | A, No color change | A | A | 91 |
| 50 | A, No color change | A | A | 91 |

As seen above, the powder compositions comprising a given amount of sodium starch octenylsuccinate with respect to reduced coenzyme $Q_{10}$ were excellent not only in powder appearance and water solubility after storage, but also in dissolution stability after storage. Additionally, the powder compositions comprising given amounts of sodium starch octenylsuccinate and also of gum arabic with respect to reduced coenzyme $Q_{10}$ were excellent not only in powder appearance and water solubility after storage, but also in dissolution stability after storage. Furthermore, the powder compositions comprising an antioxidant at a given percentage (%) by mass with respect to reduced coenzyme $Q_{10}$ were excellent in storage stability of reduced coenzyme $Q_{10}$.

Example 3: Production and Evaluation of Reduced Coenzyme $Q_{10}$-Containing Powder Compositions (2)

Reduced coenzyme $Q_{10}$-containing powder compositions were produced based on the results obtained in Example 2. That is, all the components for each test sample as indicated in Table 5 below were dissolved in 1 L of water with heating to 80° C. The resulting mixtures were then emulsified using a high-pressure homogenizer (manufactured by Sanmaru Machinery Co., Ltd.; at 500 kg/cm², 3 repeats). After the emulsification, reduced coenzyme $Q_{10}$-containing dry powder formulations were prepared using a spray dryer (Mini Spray Dryer GB22, manufactured by Yamato Scientific Co., Ltd.).

TABLE 5

Reduced coenzyme $Q_{10}$-containing powder compositions (Example 3)

| Test sample | Composition |
|---|---|
| 51 | Reduced coenzyme $Q_{10}$: 200 g<br>Sodium starch octenylsuccinate: 200 g<br>gum arabic (unmodified type): 75 g |
| 52 | Reduced coenzyme $Q_{10}$: 200 g<br>Sodium starch octenylsuccinate: 200 g<br>Gum arabic (unmodified type): 75 g<br>Sodium ascorbate: 100 g |

TABLE 5-continued

Reduced coenzyme $Q_{10}$-containing
powder compositions (Example 3)

| Test sample | Composition |
|---|---|
| 53 | Reduced coenzyme $Q_{10}$: 200 g<br>Sodium starch octenylsuccinate: 200 g<br>Gum arabic (demineralized type): 75 g |
| 54 | Reduced coenzyme $Q_{10}$: 200 g<br>Sodium starch octenylsuccinate: 200 g<br>Gum arabic (demineralized type): 75 g<br>Sodium ascorbate: 100 g |
| 55 | Reduced coenzyme $Q_{10}$: 200 g<br>Sodium starch octenylsuccinate: 200 g<br>Sodium ascorbate: 100 g |

Reduced coenzyme $Q_{10}$: manufactured by Kaneka Corporation
Sodium starch octenylsuccinate: Emulstar 500A (manufactured by Matsutani Chemical Industry Co., Ltd.)
Gum arabic (unmodified type): Inagel (manufactured by Ina Food Industry Co., Ltd.)
Gum arabic (demineralized type): San-Arabic (manufactured by Sanei-Yakuhin Co., Ltd.)
Sodium ascorbate: manufactured by DSM Japan K.K.

Each obtained reduced coenzyme $Q_{10}$-containing dry powder formulation with a weight of 10 g was placed in brown glass vials with a volume of 100 mL, three of which were degassed and purged with nitrogen gas and then sealed, and the vials were stored in a refrigerator at 5° C., a storage container at 18° C., or an incubator at 45° C. for evaluation of storage stability. Each vial was stored for two weeks to evaluate later the powder appearance (characteristics), the water solubility, the stability after dissolution in water and subsequent 8-hour standing, and the residual amount of reduced coenzyme $Q_{10}$. The powder appearance was examined by visual observation. Additionally, the water solubility and the stability after dissolution in water and subsequent 8-hour standing were classified into three grades (A: excellent, B: normal, C: bad) by visual observation. For the water solubility, a powder formulation observed to produce a solution with some suspended matters was graded B, and a powder formulation observed to produce a solution with a ring of oil was graded C. For the stability after dissolution in water and subsequent 8-hour standing, a powder formulation observed to produce a solution retaining the properties at the time of dissolution was graded A, and a powder formulation observed to produce a solution with some suspended matters was graded B, and a powder formulation observed to produce a solution with a ring of oil was graded C. Moreover, the water solubility and the stability after dissolution in water and subsequent 8-hour standing were examined by adding 0.2 g of each reduced coenzyme $Q_{10}$-containing dry powder formulation to 100 mL of water at room temperature, stirring the mixture, and then observing the resulting mixture. The storage stability of the active ingredient was evaluated based on the content ratio of reduced coenzyme $Q_{10}$ (the content ratio (%) between before and after the storage stability test). The content of reduced coenzyme $Q_{10}$ was measured by HPLC, similarly to Example 2.

The results were as shown in Tables 6 to 8.

TABLE 6

Evaluation of storage stability in reduced coenzyme $Q_{10}$-containing powder compositions

| Test sample | Storage condition (5° C.) | Powder appearance | Water solubility | Stability after dissolution in water and subsequent 8-hour standing | Content ratio of reduced coenzyme $Q_{10}$ (%) |
|---|---|---|---|---|---|
| 51 | with oxygen | Color change to yellow | A | A | 19 |
|  | with nitrogen purge | No color change | A | A | 89 |
| 52 | with oxygen | No color change | A | A | 92 |
|  | with nitrogen purge | No color change | A | A | 93 |
| 53 | with oxygen | Color change to yellow | A | A | 8 |
|  | with nitrogen purge | No color change | A | A | 88 |
| 54 | with oxygen | No color change | A | A | 90 |
|  | with nitrogen purge | No color change | A | A | 94 |
| 55 | with oxygen | No color change | B | B | 90 |
|  | with nitrogen purge | No color change | B | B | 93 |

* The test sample 55 needed more time for dissolution in water.

TABLE 7

Evaluation of storage stability in reduced coenzyme $Q_{10}$-containing powder compositions

| Test sample | Storage condition (18° C.) | Powder appearance | Water solubility | Stability after dissolution in water and subsequent 8-hour standing | Content ratio of reduced coenzyme $Q_{10}$ (%) |
|---|---|---|---|---|---|
| 51 | with oxygen | Color change to yellow | A | A | 15 |
|  | with nitrogen purge | No color change | A | A | 92 |
| 52 | with oxygen | No color change | A | A | 92 |
|  | with nitrogen purge | No color change | A | A | 93 |
| 53 | with oxygen | Color change to yellow | A | A | 14 |
|  | with nitrogen purge | No color change | A | A | 91 |
| 54 | with oxygen | No color change | A | A | 86 |
|  | with nitrogen purge | No color change | A | A | 91 |
| 55 | with oxygen | No color change | B | B | 86 |
|  | with nitrogen purge | No color change | B | B | 90 |

\* The test sample 55 needed more time for dissolution in water.

TABLE 8

Evaluation of storage stability in reduced coenzyme $Q_{10}$-containing powder compositions

| Test sample | Storage condition (45° C.) | Powder appearance | Water solubility | Stability after dissolution in water and subsequent 8-hour standing | Content ratio of reduced coenzyme $Q_{10}$ (%) |
|---|---|---|---|---|---|
| 51 | with oxygen | Color change to yellow | A | A | 10 |
|  | with nitrogen purge | No color change | A | A | 88 |
| 52 | with oxygen | No color change | A | A | 91 |
|  | with nitrogen purge | No color change | A | A | 92 |
| 53 | with oxygen | Color change to yellow | A | A | 10 |
|  | with nitrogen purge | Color change to pale yellow | A | A | 80 |
| 54 | with oxygen | Color change to pale yellow | A | A | 81 |
|  | with nitrogen purge | No color change | A | A | 91 |
| 55 | with oxygen | No color change | B | B | 81 |
|  | with nitrogen purge | No color change | B | B | 88 |

\* The test sample 55 needed more time for dissolution in water.

As seen above, the powder compositions comprising sodium starch octenylsuccinate and gum arabic at given ratios with respect to reduced coenzyme $Q_{10}$ were excellent not only in powder appearance and water solubility after storage, but also in dissolution stability after storage. Additionally, the powder compositions comprising an antioxidant at a given ratio with respect to reduced coenzyme $Q_{10}$ were excellent in storage stability of reduced coenzyme $Q_{10}$.

Example 4: Evaluation of Formulation Stability

The reduced coenzyme $Q_{10}$-containing dry powder formulations obtained in Example 3 (Test samples 51 to 55) were individually formulated into tablets according to a routine procedure, for evaluation of storage stability. Specifically, 150 mg of reduced malt sugar, 100 mg of each reduced coenzyme $Q_{10}$-containing dry powder formulation (any one of Test samples 51 to 55), 100 mg of microcrystalline cellulose, 35 mg of corn starch, 2 mg of magnesium stearate, and 2 mg of sucrose fatty acid ester were mixed, and the resulting mixture was compressed into tablets with a diameter of 8 mm and a thickness of 3.8 mm at a pressure of 14 kN. Twenty of the obtained tablets were placed in each of brown glass vials with a volume of 50 mL and were evaluated for the storage stability at the start, 2 weeks, 4 weeks, and 6 weeks of storage at 45° C. The storage stability was evaluated based on the content ratio of reduced coenzyme $Q_{10}$ (the content ratio (%) between before and after the storage stability test). The content of reduced coenzyme $Q_{10}$ was measured by HPLC, similarly to Example 2.

The results were as shown in Table 9.

TABLE 9

Storage stability of tablets

| Test sample (dry powder) | Start of storage | Week 2 | Week 4 | Week 6 |
|---|---|---|---|---|
| 51 | 100% | 51% | 26% | 17% |
| 52 | 100% | 96% | 94% | 93% |
| 53 | 100% | 48% | 30% | 15% |
| 54 | 100% | 94% | 92% | 91% |
| 55 | 100% | 83% | 80% | 78% |

As seen above, the powder compositions comprising sodium starch octenylsuccinate, gum arabic, and an antioxidant at given ratios with respect to reduced coenzyme $Q_{10}$ were excellent in storage stability of the active ingredient, reduced coenzyme $Q_{10}$. Additionally, the result from the storage stability test of the tablets containing the dry powder of Test sample 55 indicated that the presence of gum arabic as well as of an antioxidant is effective in improving the storage stability of reduced coenzyme $Q_{10}$.

What is claimed is:

1. A powder composition comprising (A) reduced coenzyme $Q_{10}$, (B) starch octenylsuccinate or a salt thereof, and (C) gum arabic,
   wherein a ratio of a solid content of said (B) starch octenylsuccinate or the salt thereof to a solid content of said (A) reduced coenzyme $Q_{10}$ is at least from 0.5 to 5 by mass.

2. The composition according to claim 1, wherein a ratio of a solid content of said (C) gum arabic to a solid content of said (A) reduced coenzyme $Q_{10}$ is 0.125 to 1 by mass.

3. The composition according to claim 1, which further comprises (D) an antioxidant.

4. The composition according to claim 3, wherein a ratio of a solid content of said (D) antioxidant to a solid content of said (A) reduced coenzyme $Q_{10}$ is 0.125 to 1 by mass.

5. The composition according to claim 3, wherein the antioxidant is ascorbic acid.

6. A reduced coenzyme $Q_{10}$-containing solid formulation, prepared from the composition according to claim 1.

7. The solid formulation according to claim 6, which is in the form of tablet, capsule, or powder.

8. A method of producing the composition according to claim 1, comprising the steps of homogenizing (A) reduced coenzyme $Q_{10}$, (B) starch octenylsuccinate or a salt thereof, and (C) gum arabic in water to obtain an emulsion composition, and drying the composition.

9. The composition according to claim 1, wherein a solid content of the reduced coenzyme $Q_{10}$ in the powder composition is from 1.0 to 50% by mass.

* * * * *

UNITED STATES PATENT AND TRADEMARK OFFICE
CERTIFICATE OF CORRECTION

PATENT NO. : 11,911,350 B2
APPLICATION NO. : 16/976616
DATED : February 27, 2024
INVENTOR(S) : Hidehiro Takahashi It is certified that error appears in the above-identified patent and that said Letters Patent is hereby corrected as shown below:

In the Claims

In Column 20, Claim 1, Line 9 (Approx.), delete "is at least from" and insert --is from--.

Signed and Sealed this
Twenty-third Day of July, 2024

Katherine Kelly Vidal
*Director of the United States Patent and Trademark Office*